(12) United States Patent
Lee et al.

(10) Patent No.: US 8,552,148 B2
(45) Date of Patent: Oct. 8, 2013

(54) TNF-α ANTAGONISTS CONTAINING IGFBP5

(75) Inventors: Je-Ho Lee, Seocho-gu (KR);
Jae-Ryoung Hwang, Gangnam-gu (KR); Jae-Ho Huh, Gangnam-gu (KR)

(73) Assignee: Sungkyunkwan University Foundation For Corporate Collaboration, Gyeonggi-do (KR)

( * ) Notice: Subject to any disclaimer, the term of this patent is extended or adjusted under 35 U.S.C. 154(b) by 219 days.

(21) Appl. No.: 13/142,700

(22) PCT Filed: Jun. 30, 2009

(86) PCT No.: PCT/KR2009/003570
§ 371 (c)(1),
(2), (4) Date: Sep. 26, 2011

(87) PCT Pub. No.: WO2010/076932
PCT Pub. Date: Jul. 8, 2010

(65) Prior Publication Data
US 2012/0046217 A1    Feb. 23, 2012

(30) Foreign Application Priority Data
Dec. 31, 2008   (KR) .................. 10-2008-0138164

(51) Int. Cl.
| | | |
|---|---|---|
| *A61K 38/00* | (2006.01) | |
| *A61K 51/00* | (2006.01) | |
| *C07K 5/00* | (2006.01) | |
| *C07K 7/00* | (2006.01) | |
| *C07K 16/00* | (2006.01) | |
| *C07K 2/00* | (2006.01) | |
| *C07K 4/00* | (2006.01) | |
| *C07K 14/00* | (2006.01) | |
| *C07K 17/00* | (2006.01) | |

(52) U.S. Cl.
USPC ............ 530/324; 530/300; 530/333; 514/1.1; 424/1.69

(58) Field of Classification Search
None
See application file for complete search history.

(56) References Cited

FOREIGN PATENT DOCUMENTS

WO    WO 97/30084 A1  *  8/1997

OTHER PUBLICATIONS

Notification Concerning Transmittal of International Preliminary Report on Patentability, and Written Opinion, with English Translations; International Application No. PCT/KR2009/003570; Date of Mailing: Jul. 14, 2011.
International Search Report, with English Translation; International Application No. PCT/KR2009/003570; Date of Mailing: Feb. 2, 2010.
Butt, A.J., et al., "Enhancement of Tumor Necrosis Factor-α-Induced Growth Inhibition by Insulin-Like Growth Factor-Binding Protein-5 (IGFBP-5), But Not IGFBP-3 in Human Breast Cancer Cells," *Endocrinology*, 146(7): 3113-3122 (2005).
Meadows, K.A., et al., "Tumor Necrosis Factor-α-Induced Apoptosis Is Associated With Suppression of Insulin-Like Growth Factor Binding Protein-5 Secretion in Differentiating Murine Skeletal Myoblasts," *J. of Cellular Physiology*, 183: 330-337 (2000).
Norgaard, J.V., et al., "Cellular Mechanisms in Regulating Mammary Cell Turnover During Lactation and Dry Period in Daily Cows," *J. Dairy Sci.*, 91: 2319-2327 (2008).

* cited by examiner

*Primary Examiner* — Maury Audet
(74) *Attorney, Agent, or Firm* — Hamilton, Brook, Smith & Reynolds, P.C.

(57) ABSTRACT

The present invention relates to: TNF-α antagonists containing IGFBP5 protein, variants thereof, or fragments thereof; and the use of the TNF-α antagonists. More specifically, the present invention relates to: a polynucleotide encoding the protein, variants thereof, or fragments thereof; a vector containing the polynucleotide; a transformant containing the vector; and a method for screening a therapeutic agent for TNF-α overexpression-related diseases by checking whether the mutual reaction thereof is facilitated after treating with candidates to the cell expressing the IGFBP5 protein, variants thereof, or fragments thereof, and the TNFR1.

1 Claim, 11 Drawing Sheets

TNF-α ANTAGONISTS CONTAINING IGFBP5

This application is the U.S. National Stage of International Application No. PCT/KR2009/003570, filed Jun. 30, 2009, which designates the U.S., published in Korean, and claims priority under 35 U.S.C. §§119 or 365(c) to Korean Application No. 10-2008-0138164, filed Dec. 31, 2008.

TECHNICAL FIELD

The present invention relates to TNF-α antagonist comprising an IGFBP5 protein, a variant thereof or a fragment thereof, and uses of the TNF-α antagonist. More particularly, the present invention relates to a TNF-α antagonist comprising an IGFBP5 protein, a variant thereof or a fragment thereof, a polynucleotide encoding the IGFBP5 protein, the variant or the fragment, a vector carrying the polynucleotide, a transformant comprising the vector, and a method for screening a therapeutic for TNF-α overexpression-related diseases by examining whether a candidate facilitates the interaction of the IGFBP5 protein, the variant thereof, or the fragment thereof with TNFR1 in a cell expressing the IGFBP5 protein, the variant thereof, or the fragment thereof, and TNFR1 after treatment with the candidate.

BACKGROUND ART

IGFBP5, a member of the IGF (insulin-like growth factor) binding protein family, is known to play an important role in various cellular functions including cell proliferation. IGFBP5 translocates to the cell nucleus due to its NLS (nuclear localization signal) and is also secreted outside the cell, but the intranuclear and extracellular functions of IGFBP5 have not yet been well studied. Recently, IGFBP5 has been reported to have transactivation activity. IGFBP5 may be largely divided into three domains (N-terminus, L-domain, and C-terminus), with the presence of an IGF binding site in the N-terminal domain, an NLS in the C-terminal domain, and a heparin binding site in both the L-domain and the C-terminal domain. Both the glycosylation and the phosphorylation of IGFBP5 are known to inhibit the heparin binding of IGFBP5, but the biological significance of the glycosylation and the phosphorylation is not well understood.

IGFBP5 modulates the functions of IGF-I and IGF-II by inhibiting the binding of IGF-I or IGF-II to their receptors while IGF-independent functions of IGFBP5 are also reported. The functions of IGFBP5 have been studied transgenic and knockout mice of IGFBP5. Increased IGFBP5 production in transgenic mice resulted in high neonatal mortality, growth inhibition and delayed muscle development. In female transgenic mice, IGFBP5 was also found to induce reduced fertility, and premature cell death in the mammary glands. IGFBP5 knockout mice demonstrated delayed mammary gland involution, reflecting the involvement of IGFBP5 in apoptosis.

TNF-α (tumor necrosis factor-alpha) is known as a pro-inflammatory cytokine which often promotes inflammatory responses and causes other diseases (e.g., septic shock due to exposure of endotoxin). TNF-α is released from macrophages, monocytes and natural killer cells and play an important role in inflammatory and immune responses. TNF-α shows the following various in vitro or in vivo effects: (i) vascular thrombosis and tumor necrosis; (ii) inflammation; (iii) activation of macrophages and neutrophils; (iv) leukocytosis; (v) apoptosis; and (vi) shock. In addition, TNF-α is associated with a variety of cancers, arthritis, psoriasis, endotoxic shock, sepsis, autoimmune diseases, infections, obesity, and cachexia.

DISCLOSURE

Technical Problem

Leading to the present invention, intensive and thorough research into a new function of IGFBP5, conducted by the present inventors, resulted in the finding that the mRNA expression of TNFR1 was increased in IGFBP5-overexpressed cells and TNFR1 was internalized into the cells co-transfected with IGFBP5 and TNFR1, indicating that IGFBP5 might act as a ligand of TNFR1. Also, our study on the interaction of IGFBP5 with TNFR1 in the presence of the TNF-α known as TNFR1 ligand, revealed that IGFBP5 acts as a competitive inhibitor of TNF-α for TNFR1 binding. Coincident with these results, the overexpression of IGFBP5 was found to inhibit the TNF-α-induced NF-κB signaling pathway. Based on the results of the research results, the present inventors suggest IGFBP5 as a therapeutic agent for TNF-α overexpression-related diseases including, inter alia, rheumatoid arthritis and caner.

Technical Solution

It is therefore an object of the present invention to provide a TNF-α antagonist comprising an IGFBP5 protein having the amino acid sequence of SEQ ID NO: 2, a variant thereof, or a fragment thereof.

It is another object of the present invention to provide a polynucleotide encoding the protein, the variant or the fragment.

It is a further object of the present invention to provide a vector carrying the polynucleotide.

It is still a further object of the present invention to provide a transformant comprising the vector.

It is still another object of the present invention to provide a composition for the treatment of TNF-α overexpression-related diseases, comprising the TNF-α antagonist.

It is yet another object of the present invention to provide a method for screening a therapeutic agent for TNF-α overexpression-related diseases, comprising treating a cell overexpressing the IGFBP5 protein, the variant thereof, or the fragment thereof, and TNFR1 with a candidate, examining whether the candidate facilitates the interaction of the IGFBP5 protein, the variant thereof, or the fragment thereof with TNFR1 in the cell, and determining the candidate as a therapeutic agent for TNF-α overexpression-related diseases if it facilitates the interaction.

Advantageous Effects

Having the functioning of blocking the binding of TNF-α to TNFR1, the composition of the IGFBP5 protein, the variant thereof or the fragment thereof in accordance with the present invention can be effective for the treatment of TNF-α overexpression-related diseases such as inflammatory diseases and cancer. In addition, the composition can be used safely without side effects of synthetic drugs because such IGFBP5 proteins are naturally present in the body.

BEST MODE

Figure 1:
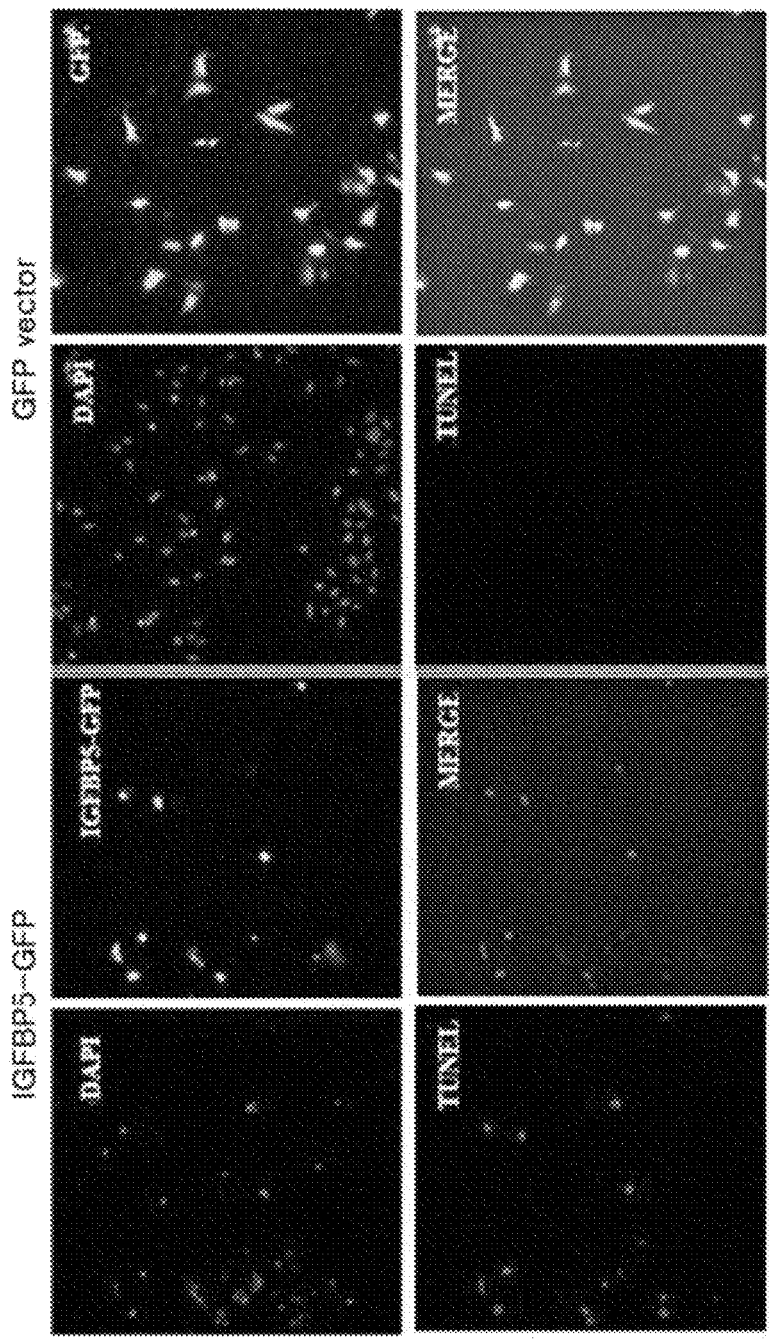
FIG. 1 is the result of TUNEL assay, which is fluorescence microphotographs of HEK293 cells after they were transiently transfected with IGFBP5-GFP or a GFP vector alone and TUNEL stained, showing IGFBP5 overexpression-induced apoptosis.

In accordance with an aspect thereof, the present invention addresses a TNF-α antagonist comprising an IGFBP5 protein having the amino acid sequence of SEQ ID NO: 2, a variant thereof, or a fragment thereof.

IGFBP5 is a member of the IGF (insulin-like growth factor) binding protein family which is known to play an important role in various cellular functions including cell proliferation. An amino acid sequence of IGFBP5 and its nucleotide sequence can be obtained from NCBI (NM_000599). IGFBP5 translocates into the cell nucleus due to its NLS (nuclear localization signal) and is also released outside the cell. However, the functions of IGFBP5 within the nucleus and outside the cell have not yet been understood well. Particularly, there is no knowledge on the extracellular functions of IGFBP5, for example, which proteins interact with IGFBP5. In this invention, it was first discovered that IGFBP5 released outside cells interacts with the membrane protein TNFR1 to inhibit the binding of TNF-α to its receptor, resulting in apoptosis.

So long as it has substantially inhibitory activity against TNF-α, any IGFBP5 variant may be used in the present invention. Preferably, the variant has a homology of 70% or higher, more preferably 80% or higher, much more preferably 90% or higher, even much more preferably 95% or higher, and most preferably 98% or higher with the IGFBP5 protein.

As used herein, the term "homology" refers to the similarity of the amino acid sequence of the variant with the wild-type protein. The amino acid sequence of the variant that falls within the scope of the present invention shares a homology of preferably 90% or higher, more preferably 95% or higher and even more preferably 98% or higher with that of SEQ ID NO: 2. The homology comparison may be done with the naked eye or using a commercially available program that can express the homology between two or more sequences as a percentage (%). The homology (%) is calculated between adjacent sequences.

Also, the present invention contemplates an amino acid sequence variant of the IGFBP5 or its homologues so long as they have substantially the same activity. In the present invention, the amino acid sequence variant refers to a protein that has an amino acid sequence different in at least one amino acid residue from the native amino acid sequence. The variant protein may have the same biological activity as the wild-type, but may differ from the wild type in physical properties. Preferably, mutations and/or modifications on the amino acid sequence may increase the structural stability of the protein to heat, pH and so on. For example, the sequence variant may show potent activity even in strong acidic or alkaline conditions where the wild-type protein becomes inactive, and may be active at low or high temperatures. In addition, mutations or modifications on the amino acid sequence may result in variants that are more specific for substrates reactive to IGFBP5 or that can react with a broader spectrum of substrates.

The fragment that is within the scope of the present invention means a part of the IGFBP5 protein or its variant. Any of the three domains (N-terminal domain, L-domain and C-terminal domain) constituting the IGFBP5 protein may be used as the fragment so long as it shows inhibitory activity against TNF-α. Preferably, the IGFBP5 fragment may be an IGFBP5 region having the amino acid sequence of SEQ ID NO: 4. To identify a region of the IGFBP5 protein that interacts directly with TNFR1, truncated mutants of IGFBP5 were constructed, and co-transfected in respective plasmid forms, together with TNFR1, into cells. As a result, it was first discovered that the practical interaction of IGFBP5 with TNFR1 is done at the mid-region L-domain rather than the N-terminal domain and the C-terminal domain.

In accordance with another aspect thereof, the present invention addresses a polynucleotide encoding the IGFBP5 protein, the IGFBP5 variant, or the fragment of IGFBP5 or IGFBP5 variant.

The term "polynucleotide," as used herein, means a nucleic acid (e.g., DNA) sequence comprising a coding sequence necessary for producing a polypeptide, a precursor or RNA (e.g. rRNA, tRNA) and is interchangeably used with a nucleic acid sequence, below. The polypeptide of the present invention may be encoded by a full-length polynucleotide or by a portion of the full-length nucleic acid so long as the complete or desired activity or some functional property (e.g, enzymatic activity, ligand binding, signal transduction, immunogenicity, etc.) may be maintained. In addition, the polynucleotide may comprise a coding region of the structural gene, and a sequence adjacent to each of the 5' and 3' termini of the coding region that is about 1 kb or greater in length corresponding to the full length of the mRNA. The 5'-untranslated region refers to a section on the 5' side of the coding sequence on a strand of mRNA while 3'-untranslated region is found on the 3' side or downstream of the coding sequence on a strand of mRNA.

The term "gene," as used herein, is intended to refer to either cDNA or genomic DNA. A clone of genomic DNA or a gene comprises a coding region interrupted by non-coding sequence such as "intron", or "insertion region" or "insertion sequence." The term "intron" refers to a gene segment transcribed into nuclear RNA (hnRNA), which may include a regulatory element, such as an enhancer, and will be removed or spliced out of the nuclear or primary transcript. Therefore, an intron is absent from an mRNA transcript. During translation of mRNA, mRNA functions to determine the amino acid sequence or order of a primary polypeptide.

Gene expression is the process by which information from a gene is converted into RNA (e.g., mRNA, rRNA, tRNA or snRNA) through transcription (by, for example, the enzymatic action of RNA polymerase) and then into a protein through the "translation" of mRNA. Gene expression may be regulated at many steps in the entire process. The term "up-regulation" or "activation" refers to an increase in the level of a gene expression product while the term "down-regulation" or "suppression" refers to a decrease in the level. A molecule associated with up-regulation or down-regulation (e.g., a transcription factor) is often called an "activator" or "suppressor," respectively. A gene in a genomic form may comprise a sequence on either of the 5' or the 3' side of an RNA transcript in addition to an intron. This sequence is called a "flanking" sequence or region (it is adjacent to the 5' or 3' end of the untranslated region of the RNA transcript). A 5' flanking region may comprise a regulatory element that regulates or influences the transcription of the gene, such as a promoter and an enhancer while sequences directing the termination of transcription, post-transcriptional cleavage and polyadenylation may be found in a 3' flanking region.

The polynucleotide of the present invention means a nucleic acid sequence coding for the IGFBP5 protein, the IFGBP variant, or the fragment thereof, and may further comprise a sequence necessary for the expression of the coding sequence. Preferably, the IGFBP5 polynucleotide of the present invention may have the nucleotide sequence of SEQ ID NO. 1. Optionally, a polynucleotide encoding the IGFBP5 variant or the fragment may be useful in the present invention so long as it guarantees the inhibitory activity against TNF-α. Preferably, the nucleotide sequence of SEQ ID NO: 3 for the fragment may be employed in the present invention.

In accordance with a further aspect thereof, the present invention pertains to a vector carrying the polynucleotide.

The term "vector," as used herein, refers to an expression vector that can express a protein of interest in a suitable host cell. In this context, the vector is constructed such that essential regulatory elements are operably linked together to express a gene insert. The vector may be derived from plasmids, bacteriophages, or plant or animal viruses, and the nucleic acid sequence necessary for gene expression may comprise a promoter, an operator, and a ribosome binding site for prokaryotes or a promoter, an enhancer, and a termination and polyadenylation signal for eukaryotes in addition to the polynucleotide sequence coding for the target protein or the variant or fragment thereof.

The term "operably linked," as used herein, refers to the linkage of the regulatory elements with a nucleic acid sequence encoding the target protein in such a functional relationship that the elements can operate to express the target protein. For example, a promoter may be operably linked to a nucleic acid encoding a protein or RNA so that the expression of the coding sequence can be done. A recombinant vector in which regulatory elements and a coding sequence are operably linked together may be constructed using a typical genetic recombination technique. Site-specific DNA cleavage and linkage may be done with enzymes well known in the art.

An appropriate expression vector comprises regulatory elements such as a promoter, an initiation codon, a termination codon, a polyadenylation signal and an enhancer, and may be constructed into various types depending on their purpose. Both the initiation codon and the termination codon have to function in a subject to which the gene construct is administered and be in frame with the coding sequence.

Preferably, a vector comprising a sequence encoding the IGFBP5 protein, the variant or the fragment thereof according to the present invention was constructed. In detail, the expression vector IGFBP5-Myc-His or IGFBP5-GFP was constructed to identify the expression pattern and function of IGFBP5, and transfected into cells to analyze the interaction of IGFBP5 with other proteins. In addition, an examination was made to see whether IGFBP5 competes with TNF-α for TNFR1. In this regard, a vector comprising a Flag-TNFR1 structure was constructed and co-transfected, together with the IGFBP5-Myc vector. As a result, IGFBP5 was found to interact with TNFR1, thus suppressing the activity of TNF-α.

In accordance with still a further aspect thereof, the present invention pertains to a transformant anchoring the vector.

So long as it can introduce a nucleic acid sequence of interest into prokaryotic or eukaryotic host cells, any transfection technique may be employed. A suitable typical technique well known in the art may be selected depending on the type of host cells. Examples of the transfection technique useful in the present invention may include electroporation, plastogamy, calcium phosphate ($CaPO_4$) precipitation, calcium chloride ($CaCl_2$) precipitation, silicon carbide-mediated transfection, agrobacterium-mediated transfection, and transfection using PEG, dextran sulfate, lipofectamine, or viral vector, but are not limited thereto.

A suitable host cell may be an autologous or a foreign animal cell. In an embodiment of the present invention, IGFBP5-Myc-His was transfected into an HEK (Human Embryonic Kidney) 293 cell line to yield BP5/293 cells.

TNF is primarily produced by T-lymphocytes and macrophages when they are activated by the infection of a foreign antigen. TNF binds to TNFR1 to activate the transcription factor NF-κB, which, in turn, induces the expression of genes involved in inflammatory and immune responses. When activated by TNF-α, p65, a subunit of NF-κB, translocates into the nucleus and promotes the transcription of genes involved in cell growth. TNF-α is reported to induce cell growth or death depending on the types of tissues or the concentrations thereof. In this context, we found that IGFBP5 can induce apoptosis under the condition where TNF-α stimulates cell growth. In detail, IGFBP5 interacts with TNFR1 to induce apoptosis. The IGFBP5 protein having the amino acid sequence of SEQ ID NO: 2, the variant thereof, or the fragment thereof in accordance with the present invention competes with TNF-α for TNFR1, thus acting as a TNF-α antagonist to inhibit the binding of TNF-α to TNFR1.

The IGFBP5 protein having the amino acid sequence of SEQ ID NO: 2, the variant thereof or the fragment thereof in accordance with the present invention can inhibit the binding of TNF-α to TNFR1 to suppress the activation of NF-κB. In greater detail, the IGFBP5 protein having the amino acid sequence of SEQ ID NO: 2, the variant thereof or the fragment thereof in accordance with the present invention suppress the activation of NF-κB to block the nuclear translocation of p65. Thus, the IGFBP5 protein, the variant thereof or the fragment thereof in accordance with the present invention suppresses TNF-α-induced cell growth in the presence of TNFR1 on the cell membrane while switching on an apoptosis pathway to induce cell death.

In accordance with still another aspect thereof, the present invention pertains to a composition for the treatment of TNF-α overexpression-related diseases, comprising the TNF-α antagonist.

When binding to TNFR1, the IGFBP5 protein having the amino acid sequence of SEQ ID NO: 2, the variant thereof or the fragment thereof in accordance with the present invention blocks the interaction of TNF-α with TNFR1, thus being curative of diseases caused by the expression of TNF-α.

As used herein, the term "apoptosis" refers to the process of programmed cell death (PCD) by which biochemical events including chromatin condensation, and cell shrinkage take place to form an apoptotic body while the cell membrane and small organelles are maintained normally. Apoptosis is discriminated from necrosis in which the cell membrane and cytoplasm change morphologically. The cell undergoing apoptosis is characterized by DNA fragmentation, that is, the random cleavage of chromatin DNA into internucleosomal fragments. DNA fragmentation is often analyzed using agarose gel electrophoresis to demonstrate a "ladder" pattern at about 200-bp intervals. The death of cells by apoptosis depends on the synthesis of new proteins within the same cells. A gene that induces apoptosis is called a "suicide gene." There are various processes that lead a cell to apoptosis. For example, membrane receptors of several ligands, such as Fas antigen, TNF, etc., can mediate signals leading to apoptosis of the cell. Cell death plays an important role in the morphogenetic progression of ontogenesis and in the homeostatic maintenance of adult individuals. Cell death is presumed to be genetically precisely programmed (programmed cell death) and appears in an apoptotic pattern in most cases. The composition of the present invention comprising an IGFBP5 protein or a variant or fragment thereof having substantially the same biological activity as IGFBP5 blocks a TNF-α induced signal transduction pathway, finally promoting the apoptosis of the cells. More preferably, the composition of the present invention comprising an IGFBP5 protein or a variant or fragment thereof can be administered to a subject, thereby to prevent or treat the diseases caused by the expression of TNF-α thanks to its function of blocking the INF-α-induced signal transduction pathway.

Among the TNF-α overexpression-related diseases are all of the diseases known to be caused by the overexpression of TNF-α, and examples of the diseases include rheumatoid arthritis, juvenile rheumatoid arthritis, osteoarthritis, spondyloarthropathies, inflammatory bowel disease, chronic heart failure, diabetes mellitus, systemic lupus erythematosus, scleroderma, sarcoidosis, Crohn's Disease, psoriasis, polymyositis/dermatomyositis, multiple myeloma, myelodysplastic syndrome, acute myelogenous leukemia, Parkinson's disease, AIDS dementiacomplex, Alzheimer's disease, depression, sepsis, pyoderma gangrenosum, hematosepsis, septic shock, Behcet's syndrome, graft-versus-host disease, uveitis, Wegener's granulomatosis, Sjogren's syndrome, chronic obstructive pulmonary disease, asthma, acute pancreatitis, periodontal disease, cachexia, central nervous system injury, cancer (e.g., lung carcinomas, esophagus carcinoma, gastric adenocarcinoma, and prostate carcinoma), viral respiratory disease, and obesity, but are not limited thereto. Preferably, the TNF-α overexpression-related disease is an inflammatory disease in which TNF-α acts as a potent inducer.

In a preferred embodiment, the composition of the present invention may further include at least one pharmaceutically acceptable carrier or excipient in addition to IGFBP5.

The term "pharmaceutically acceptable," as used herein, is intended to mean suitable for administration to mammals including humans in the context of toxicity or safety. Examples of the carrier useful in the present invention include a dilution, an excipient, a filler, a binder, a wetting agent, a disintegrant, an absorption improver, a surfactant, a absorbent carrier, a lubricant and other agents commonly usable in the pharmaceutical field. If necessary, a flavor or a sweetener may be added. The composition may also comprise other pharmaceutically acceptable excipients useful for changing physical conditions such as pH, osmotic pressure, viscosity, asepsis, lipid content, solubility, etc. A pharmaceutically acceptable excipient that allows the active ingredient to be released in a sustained or delayed manner may be also contained in the composition.

Examples of a suitable excipient include water, saline, dextrose, glycerol, ethanol and the like. If desired, the pharmaceutical composition may comprise a small amount of a non-toxic aid such as a wetting agent, an emulsifier, or a pH buffer, e.g., sodium acetate, sorbitan monolaurate, triethanolamine oleate, triethanamine sodium acetate, etc.

The composition of the present invention may be administered via a systemic or oral route. A preferred dosage form for systemic administration is an injection including, inter alia, an intravenous injection. Also, other injection routes, such as subcutaneous, intramuscular or intraperitoneal routes, may be employed. Alternatives of the systemic administration include transmucosal and transdermal administration using penetrants such as bile acid, fucidic acid, a surfactant, etc. Also, the polypeptide or the composition of the present invention may be formulated into an enteric coating, a capsule, or an oral agent. Further, the composition of the present invention may be topically and/or locally administered in the form of an ointment, paste, or gel.

In an embodiment, the composition of the present invention may comprise a liposome. A liposome suitable for use in pharmaceutical administration is a DOTAP:cholesterol nanoparticle.

When the composition of the present invention comprises a nucleic acid, the nucleic acid may be delivered by a vector. For example, the vector may be a viral vector. In a certain embodiment, the viral vector is an adenovirus vector. In an embodiment, the adenovirus may be formulated, together with protamine. A number of viral particles may be administered to a patient. According to an embodiment, the composition may be administered at a dose of about $10^8$ to $10^{14}$ viral particles per dosage to a patient.

In an embodiment of the present invention, the composition comprising a nucleic acid may further include at least one lipid. Any lipid may be used for forming the lipid-nucleic acid composition. Examples of the lipid include DOTAP, cholesterol or derivatives thereof.

The term "therapeutically effective amount," as used herein, refers to an amount of the active ingredient such as IGFBP5 at which a desired therapeutic effect or response can be elicited or a desired benefit can be provided when the composition is administered according to a predetermined regimen. The practical dosage of the composition may be determined by attending physicians on the basis of various factors including the severity of disease, dosage forms, patient's age, weight, and response, the route of administration, etc.

In accordance with yet another aspect thereof, the present invention pertains to a method for screening a therapeutic agent for TNF-α overexpression-related diseases by examining whether a candidate facilitates the interaction of the IGFBP5 protein, the variant thereof, or the fragment thereof with TNFR1 in a cell expressing the IGFBP5 protein, the variant thereof, or the fragment thereof, and TNFR1 after treatment with the candidate.

Preferably, the screening method comprises a) treating a cell expressing the IGFBP5 protein, the variant thereof, or the fragment thereof, and TNFR1 with a candidate; b) examining whether the candidate facilitates the interaction of the IGFBP5 protein, the variant thereof, or the fragment thereof with TNFR1 in the cell; and c) determining the candidate as a therapeutic agent for TNF-α overexpression-related diseases if it facilitates the interaction.

The cell of step a) may be a cell line expressing the IGFBP5 protein, the variant thereof, or the fragment thereof, and TNFR1 due to its natural function or may be a cell which has been artificially converted using a typical expression technique from one naturally expressing either or none of the proteins into one expressing both of them. Also, the cell naturally expressing both of them may be genetically manipulated such that it can overexpress the proteins. The typical expression technique may be carried out by introducing a gene construct such as an expression vector into a cell. Any technique may be used so long as it allows the expression of a protein of interest within cells.

After both IGFBP5 and TNFR1 are induced to be expressed within a cell, IGFBP5 is secreted outside the cell and acts as a ligand to the TNFR1 located on the cell membrane. As elucidated in the present invention, IGFBP5 serves as a ligand in competition with TNF-α for TNFR1 and thus can regulate the TNF-α-induced downstream signaling, resulting in the blockage of TNF-α signal pathway. Hence, a substance that facilitates the interaction of IGFBP5 with TNFR1, if identified, may be used as a therapeutic agent for diseases caused by TNF-α overexpression.

Usual methods for detecting protein interactions may be employed for determining whether the interaction of IGFBP5 with TNFR1 is facilitated in step b), without limitations. For example, respective antibodies to the proteins may be used. Preferably, the antibodies can respectively recognize the interaction motifs present on IGFBP5 and TNFR1.

No particular limitations are imparted to the type of the antibodies. The antibodies may be monoclonal or polyclonal. Alternatively, any protein may be used as the antibody so long as it has an antigen-binding property. Among the antibodies used in the present invention are all immunoglobulin antibodies. Further, special antibodies such as humanized antibodies may be used in the present invention. Moreover, the antibodies useful in the present invention may be in an intact form comprising two full-length light chains and two full-length heavy chains or may be functional fragments of antibody molecules so long as it can detect the expression level and expression site of IGFBP5 and TNFR1, respectively. The term "functional fragments of antibody molecules" refers to fragments retaining at least an antigen binding function, as illustrated by Fab, F(ab'), F(ab')$_2$ and Fv.

When these antibodies are employed, the protein of interest may be quantitatively analyzed by determining the level of the antibodies bound to the antigens. Examples of the quantitative assays include Western blotting, ELISA (enzyme linked immunosorbent assay), RIA (Radioimmunoassay), radioimmunodiffusion, Ouchterlony immune diffusion, rocket immunoelectrophoresis, histoimmunostaining, Immunoprecipitation assay, complement fixation assay, FACS and protein chip assay, but are not limited thereto.

When IGFBP5 or TNFR1 is introduced into a cell by transfection, a purification tag for subsequent detection may be inserted into the corresponding sequence so that interaction between the two proteins can be readily detected. Examples of the purification tags include glutathione S-transferase (Pharmacia, USA), maltose binding protein (NEB, USA), FLAG (IBI, USA) and 6×His (hexahistidine; Quiagen, USA), with the greatest preference for 6×His (hexa histidine), but are not limited thereto. In a preferred embodiment of the present invention, IGFBP5 and TNFR1 were tagged with Myc and FLGS, respectively before the transfection of the vector. These tags were used to observe the expression and the location of the proteins inside (or outside) cells, confirming that IGFBP5 is released extracellularly and binds to TNFR1 on the cell membrane.

MODE FOR INVENTION

A better understanding of the present invention may be obtained through the following examples which are set forth to illustrate, but are not to be construed as limiting the present invention.

Example 1

Construction of Recombinant Vectors
IGFBP5-Myc-His and IGFBP5-GFP

Figure 14:
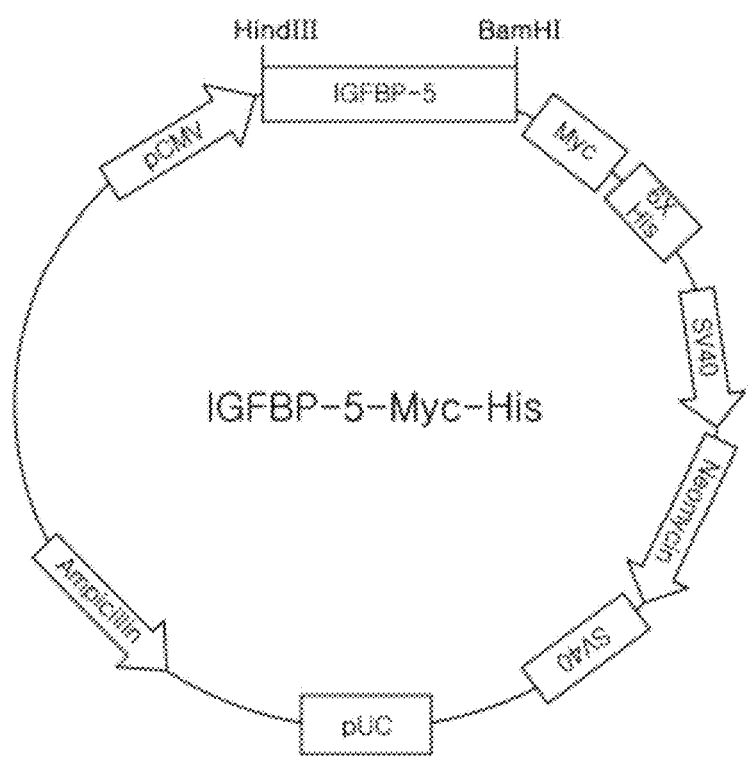
FIG. 14 shows the structure of the recombinant vector IGFBP5-Myc-His constructed according to an embodiment.
Figure 15:
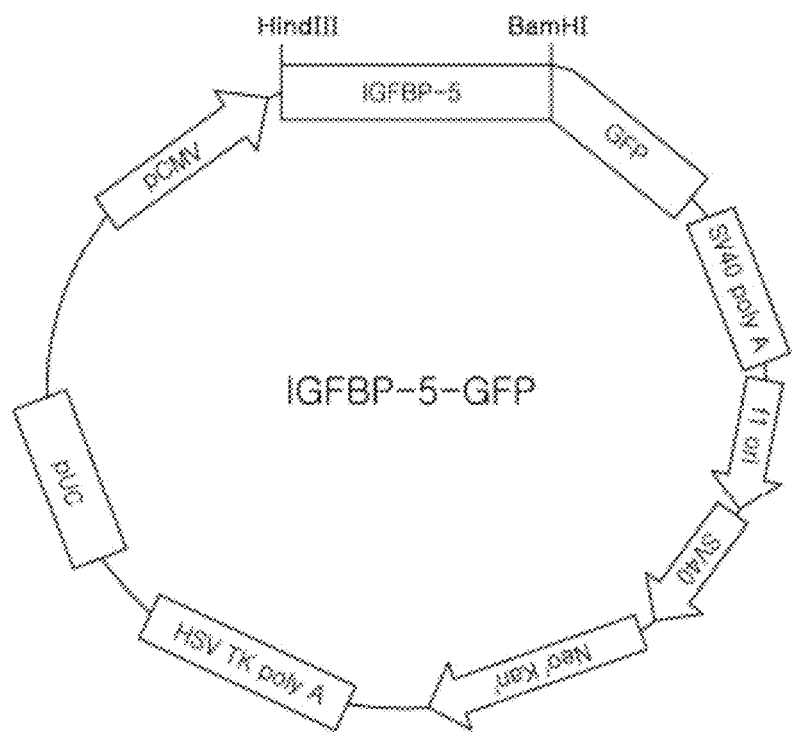
FIG. 15 shows the structure of the recombinant vector IGFBP5-GFP constructed according to an embodiment.

An IGFBP5 gene (cDNA) was prepared by extracting RNA from the HEK293 cell line (ATCC) and performing RT-PCR in the presence of primers (BP5F: 5'-CCGCAAGCTTATG-GTGTTGCTCACCGC-3'; BP5R: 5'-GCCCGGATC-CATCTCAACGTTGCTGCT-3'), with the RNA serving as a template. The IGFBP5 gene was cloned separately into pcDNA3.1/myc-His version C (Invitrogen) and pEGFP-N1 (Clontech) at the HindIII and BamHI site to construct IGFBP5-Myc-His (FIG. 14) and IGFBP5-GFP plasmids (FIG. 15), respectively. Amino acid sequencing confirmed the cloning of the IGFBP5 gene devoid of mutations. The nucleotide and amino acid sequences of IGFBP5 were defined as SEQ ID NOS: 1 and 2, respectively.

Example 2

Induction of Cell Death by IGFBP5 Overexpression

Figure 2:
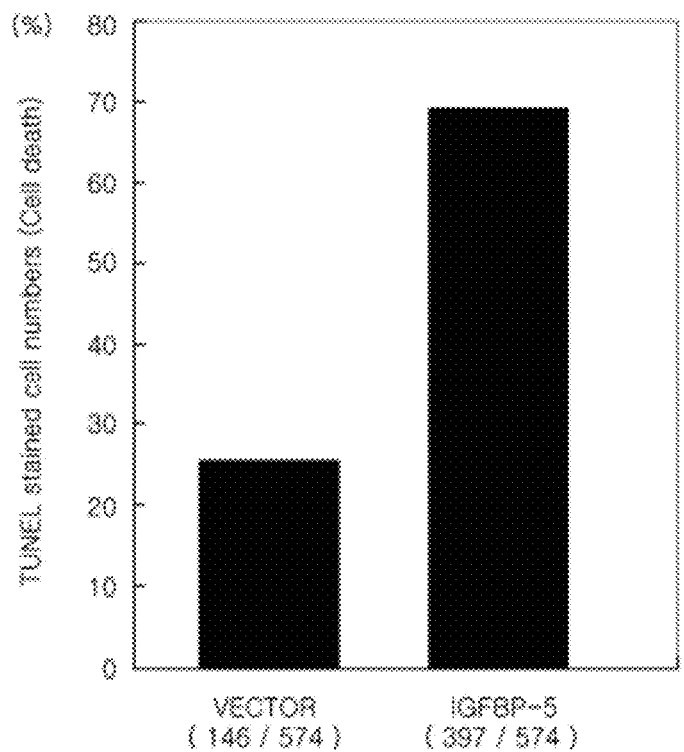
FIG. 2 is a bar graph showing counts of the cells which were TUNEL stained as percentages of the total number of cells.

To examine the function of IGFBP5, IGFBP5-GFP was overexpressed by transient transfection into HEK293 cells which were then analyzed for cell death by TUNEL staining. The TUNEL assay was performed as follows. After being incubated for 24 hours on gelatin-coated cover glass in 6-well plates, HEK293 cells were transiently transfected with IGFBP5-GFP in an amount of 400 ng per well with the aid of Effectene (Qiagen) while a GFP mock vector served as a control. Twenty four hours after transfection, the cells were washed twice with 2 mL of 1×PBS and fixed at room temperature for 10 min with 2 mL of 4% paraformaldehyde. After three washes with PBS, the cells were stained at 37° C. for 1 hour with a TUNEL solution (Roche—In Situ Cell Death Detection Kit, TMR red). After completion of the staining, the cells were washed twice with 2 mL of PBS, and the cover glass was attached onto a slide by a mounting reagent and sealed with a manicure agent before observation under a fluorescence microscope (FIG. 1). The TUNEL-positive (red) cells that expressed GFP (green) were counted (FIG. 2). A greater number of the cells expressing IGFPB5-GFP were observed to undergo apoptosis than those transfected with the GFP vector, indicating that IGFBP5 is involved in apoptosis.

Example 3

IGFBP5 Overexpression-Induced mRNA Expression of TNFR1 and Apoptosis

Figure 3:
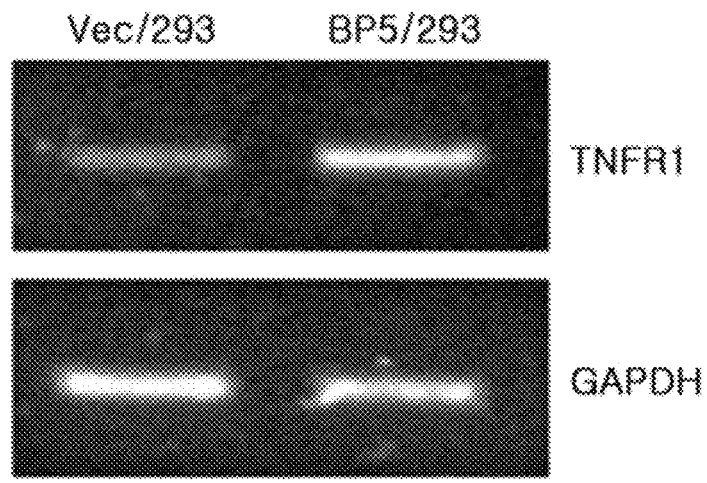
FIG. 3 shows RT-PCR results of TNFR1 in IGFBP5/293 and Vec/293 cells.

For use in studying the mechanism by which IGFBP5 induces apoptosis, an HEK293 cell line overexpressing IGFBP5 (BP5/293) was prepared by cloning Myc-tagged IGFBP5 and stably transfecting the clone into HEK293 cells. To examine the gene expression pattern of the BP5/293 cell line through a cDNA microarray assay, total RNA was isolated using Trizol (Invitrogen) according to the instruction of the manufacturer. After quantitative and qualitative analysis, the total RNA was entrusted to Genomic Tree for cDNA microarray assay. The RNA extracted from the HEK293 cells transfected with a Myc-vector alone was used as a control. Expression changes were observed in many genes. Inter alia, TNFR1 was increased in expression level. This result was confirmed by RT-PCR (reverse-transcription PCR) (FIG. 3). The RT-PCR of TNFR1 was performed by reverse transcribing 3 μg of the total RNA into cDNA in the presence of SuperScriptII (Invitrogen), followed by performing PCR with a pair of primers (TNFR1 F: 5'-GTGCACCTGCCATG-CAGGTTTCTT-3' and TNFR1 R: 5'-TGTCCTCCCACT-TCTGAAGGGGGT-3') in the presence of an EF Tag polymerase (Solgent, Korea) according to the protocol of the manufacturer. The thermal cycle program is as follows.

| *TNFR1 | | *GAPDH | |
|---|---|---|---|
| 95° C. 2 min | | 95° C. 2 min | |
| 95° C. 20 sec | } 30 cycles | 95° C. 20 sec | } 25 cycles |
| 65° C. 40 sec | | 55° C. 40 sec | |
| 72° C. 1 min | | 72° C. 1 min | |
| 72° C. 5 min | | 72° C. 5 min | |
| 4° C. ∞ | | 4° C. ∞ | |

As a quantitative control for cDNA, GAPDH was subjected to RT-PCR according to the PCR program suggested above.

Example 4

Assay of IGFBP5 for Specific Interaction with TNFR1

Figure 4:
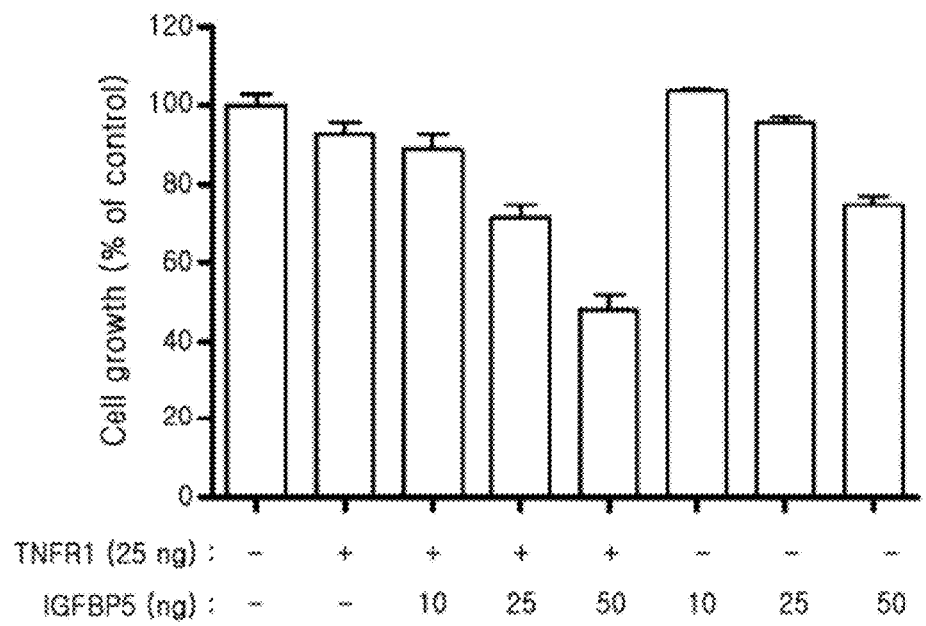
FIG. 4 shows IGFBP5-induced TNFR1-dependent apoptosis as results of an MTT assay conducted 72 hours after the co-transfection of HEK293 cells with respective vectors carrying IGFBP5 and TNFR1.
Figure 5:
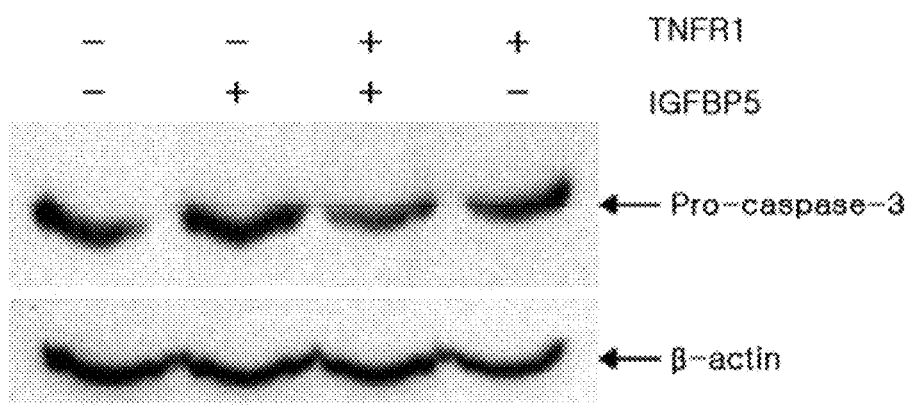
FIG. 5 shows the level of caspase 3 in HEK293 cell lysates as a result of Western blotting analysis after co-transfection with IGFBP5 and TNFR1.

To evaluate the effect of TNFR1 expression on IGFBP5-induced apoptosis, TNFR1 and IGFBP5 were co-transfected into HEK293 which was then incubated for 72 hours before an MTT assay was carried out to measure apoptosis (FIG. 4). The amount of IGFBP5 was increased with the amount of TNFR1 plasmid fixed at a constant level. A greater number of the cells expressing both IGFBP5 and TNFR1 were observed to undergo apoptosis than did the cells expressing IGFBP5 alone. Further, the count of the cells undergoing apoptosis increased with the concentration of IGFBP5. Therefore, it was found that the apoptosis effect caused by IGFBP5 could be enhanced by the expression of TNFR1. These results were supported by measuring the activity of caspase 3, that is, the degradation of pro-caspase 3 into caspase 3. The co-transfection of IGFBP5 and TNFR1 decreased the level of pro-caspase 3, that is, increased the degradation of pro-caspase 3, compared to the transfection of IGFBP5 alone (FIG. 5).

Example 5

Identification of the Domain of IGFBP5 Interacting with TNFR1

Figure 6:
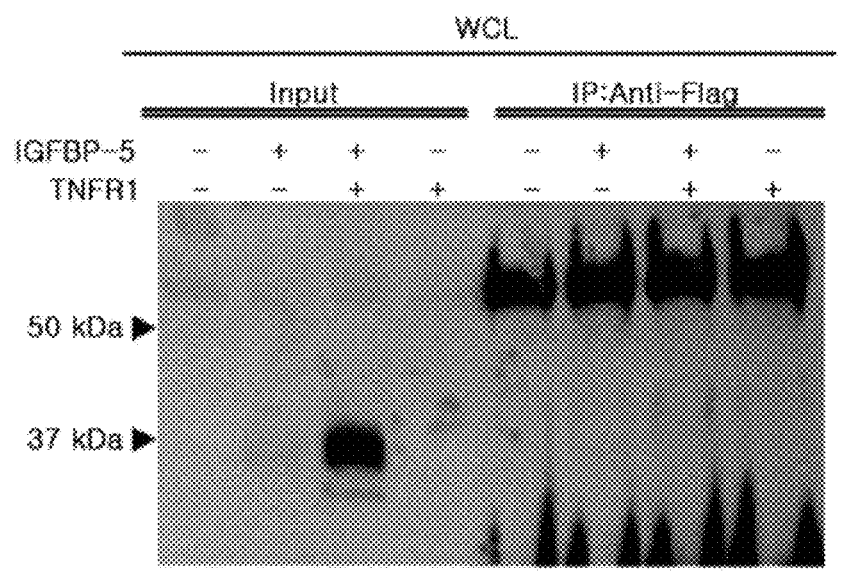
FIG. 6 shows interaction between IGFBP5 and TNFR1 as a result of immunoprecipitation in cell lysates obtained after HEK293 cells were co-transfected with IGFBP5-Myc and Flag-TNFR1.
Figure 7:
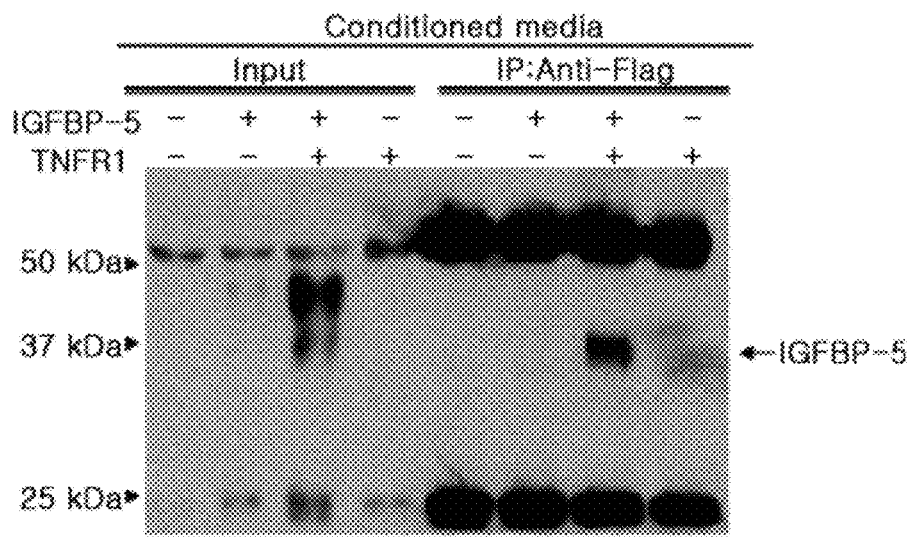
FIG. 7 shows interaction between IGFBP5 and TNFR1 as a result of immunoprecipitation in media.

To examine interaction between IGFBP5 and TNFR1, IGFBP5-Myc and Flag-TNFR1 were co-transfected into HEK293 cells. Thirty six hours after transfection, the cells were lyzed with RIPA buffer and the whole cell lysate was subjected to co-immunoprecipitation with a Flag antibody. Because IGFBP5 is a secreted protein, it was also co-immunoprecipiated with a conditioned medium. For this co-immunoprecipitation in a condition medium, the medium used for transfection was removed 24 hours after transfecion, and the cells were washed with PBS and treated with a 1/10,000 dilution of anti-Flag in Opti-MEM for 8 hours in a 37° C. incubator. Interaction between IGFBP5 and TNFR1 was observed in the conditioned medium, but not in the whole cell lysate of HEK293 (FIGS. 6 and 7). The interaction in the conditioned medium accounted for the fact that IGFBP5 was secreted and bound to TNFR1 located on the cell membrane, suggesting that IGFBP5 acts as a TNFR1 ligand.

Figure 8:
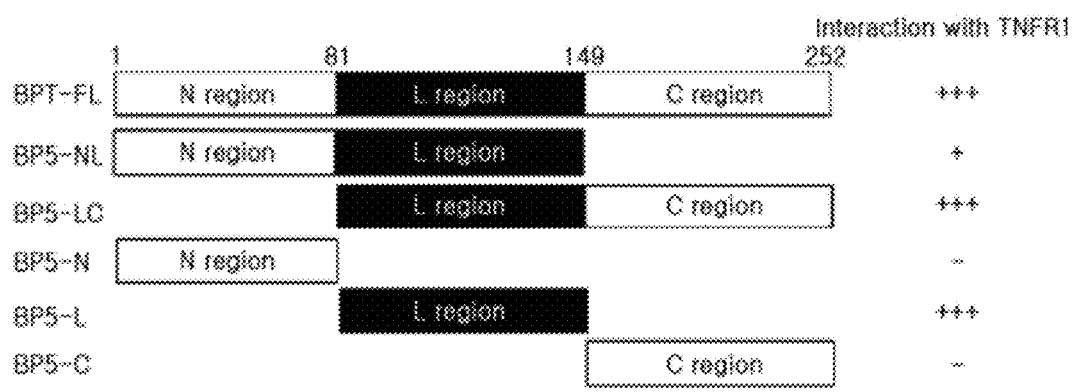
FIG. 8 is a schematic diagram showing the three domains of IGFBP5 and results of analyzing the region which interacts with TNFR1.

To map the TNFR1-interacting region of IGFBP5, truncated mutants of IGFBP5 were constructed using PCR (FIG. 8), as follows: while the IGFBP5-Myc plasmid served as a PCR template, a pair of primers BP5N5' (5'-CCGCAAGCT-TGCTGGGCTCCTTCGTGCACT-3') and BP5N3' (5'-GC-CCCTCGAGGGCAAACCCCGCGGCCGTGC-3') were used for constructing a truncated mutant consisting of an IGFBP5 N-terminal domain, a pair of primers BP5L5' (5'-CCGCAAGCTTGCTCAACGAAAAGAGCTACC-3') and BP5L3' (5'-GCCCCTCGAGGCTCAGACTCCTGTCT-CATC-3') for a truncated mutant consisting of an IGFBP5 L-domain, and a pair of primers BP5C5' (5'-CCGCAAGCT-TGCAGGGCCCCTGCCGCAGAC-3') and BP5C3' (5'-GC-CCCTCGAGGCTCAACGTTGCTGCTGTCG-3') for a truncated mutant consisting of an IGFBP5 C-terminal domain. Because the IGFBP5 gene is GC-rich, in order to increase the efficiency of denaturation, a mixture of all PCR components except for Taq polymerase was heated at 95° C. for 15 min and incubated for 5 min in ice water. In the presence of EF-Taq DNA polymerase (Solgent, Korea), the mixture was subjected to PCR with 25 cycles of the following PCR program

| 95° C. 20 sec | |
|---|---|
| 58° C. 40 sec | } 25 cycles |
| 72° C. 1 min | |
| 72° C. 5 min | |
| 4° C. ∞ | |

The PCR products thus obtained were cloned into a pSec-Taq2/Hygro A (Invitrogen) vector and confirmed by base sequencing.

Figure 9:
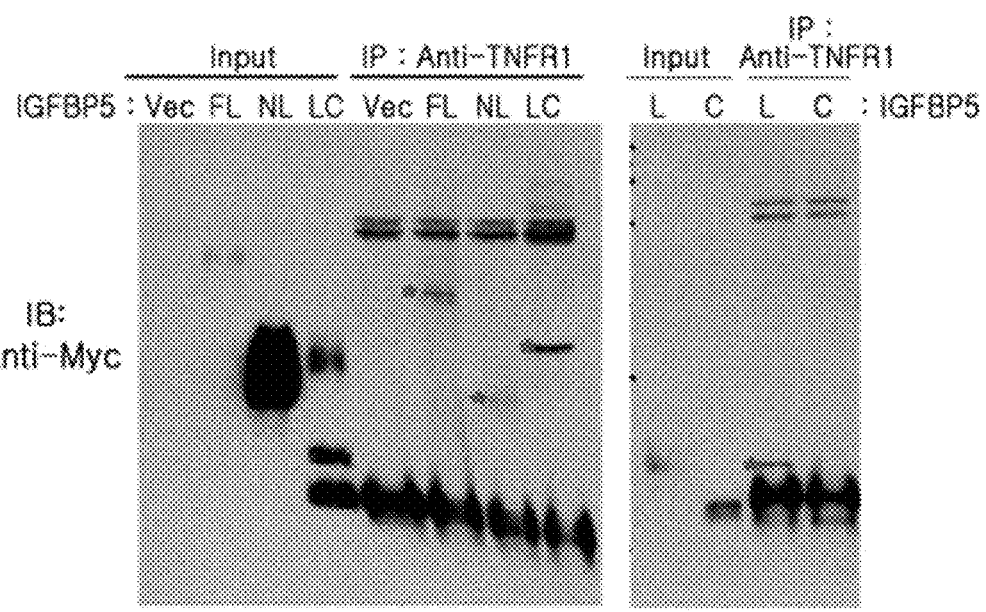
FIG. 9 shows the interaction of each of the truncated mutants of IGFBP5 with TNFR1 as a result of measurement in conditioned media to examine whether the interaction of TNFR1 is IGFBP5-specific.

Twenty four hours after respective plasmids carrying the truncated mutants of IGFBP5 were co-transfected, together with TNFR1, into HEK293 cells, the cells were washed with PBS and incubated for 8 hours with a 1/10,000 dilution of an TNFR1 antibody in Opti-MEM medium. The cells were washed with RIPA buffer, and protein-A/G-agarose beads (Santa Cruz) were added in an amount of 20 μL/tube to perform immunoprecipitation. According to the molecular weights of the truncated mutants, or 15% SDS-PAGE gel electrophoresis was carried out, followed by Western blotting with an Myc antibody (FIG. 9). As shown, the interaction region of IGFBP5 with TNFR1 was identified as the L-domain.

Example 6

IGFBP5 As a Novel TNFR1 Ligand

Figure 10:
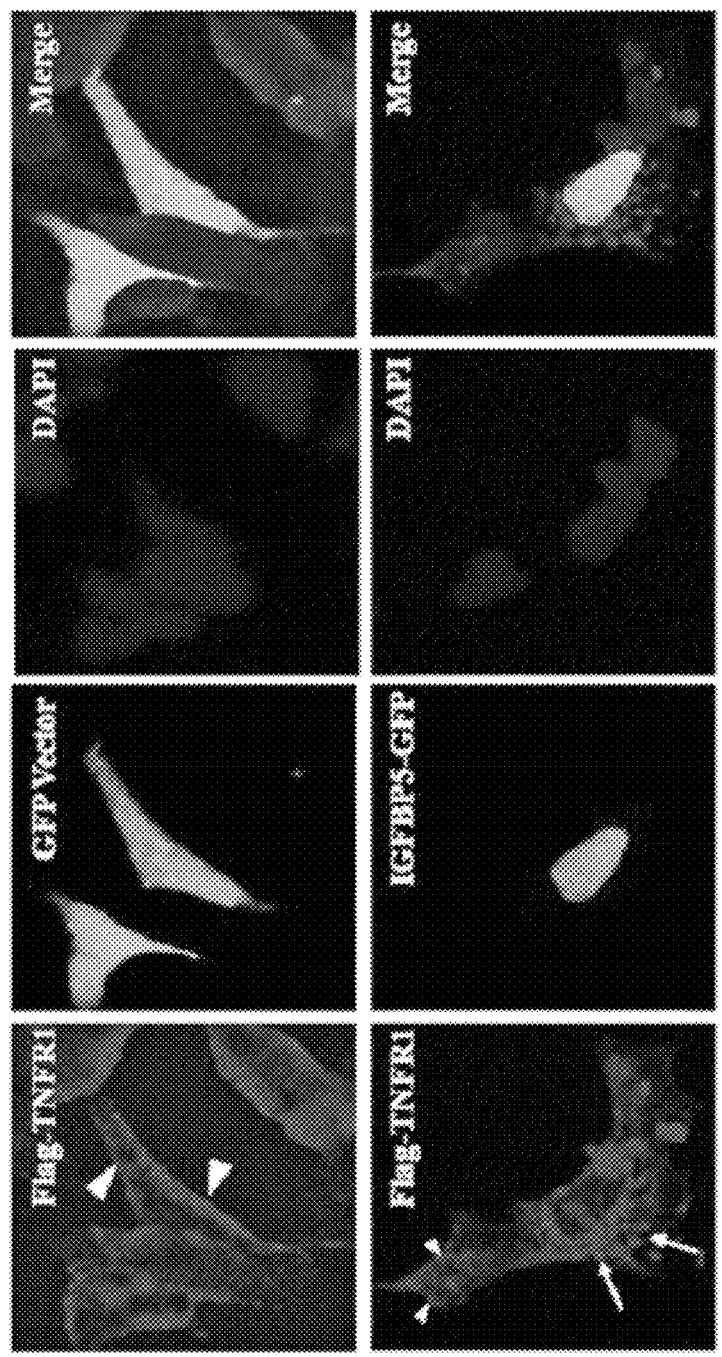
FIG. 10 shows IGFBP5-induced TNFR1 internalization as a result of confocal microscopy.

The interaction of the secreted IGFBP5 with TNFR1 indicates the likelihood that IFGBP5 might act as a TNFR1 ligand. It is known that the binding of a ligand to a receptor induces the internalization of the receptor into the cell. Accordingly, IGFBP5-induced internalization of TNFR1 was examined. Flag-TNFR1 was transfected alone or in combination with IGFBP5-GFP into HEK293 cells which were then stained with anti-Flag before confocal microscopy. TNFR1 was internalized into the cells expressing IGFBP5-GFP whereas TNFR1 was observed to be located on the cell membrane of the cells transfected with TNFR1 alone (FIG. 10). Hence, the results suggest that IGFBP5 acts as a TNFR1 ligand.

Example 7

IGFBP5 as a Competitive Inhibitor of TNF-α

Figure 11:
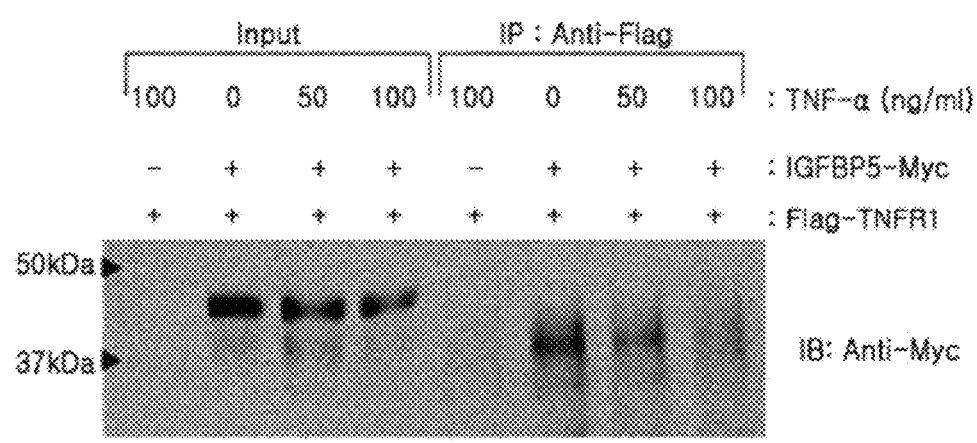
FIG. 11 shows the inhibition of TNF-α against interaction between IGFBP5 and TNFR1.

To examine the effect of IGFBP5 on the TNFR1 ligand TNF-α, Flag-TNFR1 and IGFBP5-Myc plasmids were co-transfected into HEK293 cells which were incubated for 8 hours with an anti-TNFR1 (1/10,000 dilution) at TNF-α concentrations of 0, 25, 50, and 100 ng/ml. The media were collected and treated with protein-A/G beads for immunoprecipitation, followed by Western-blotting assay. As can be seen in FIG. 11, the amount of IGFBP5 which interacted with TNFR1 was reduced with increasing concentration of TNF-α applied to the cells. This result indicates that IGFBP5 competes with TNF-α for TNFR1-binding.

Figure 12:
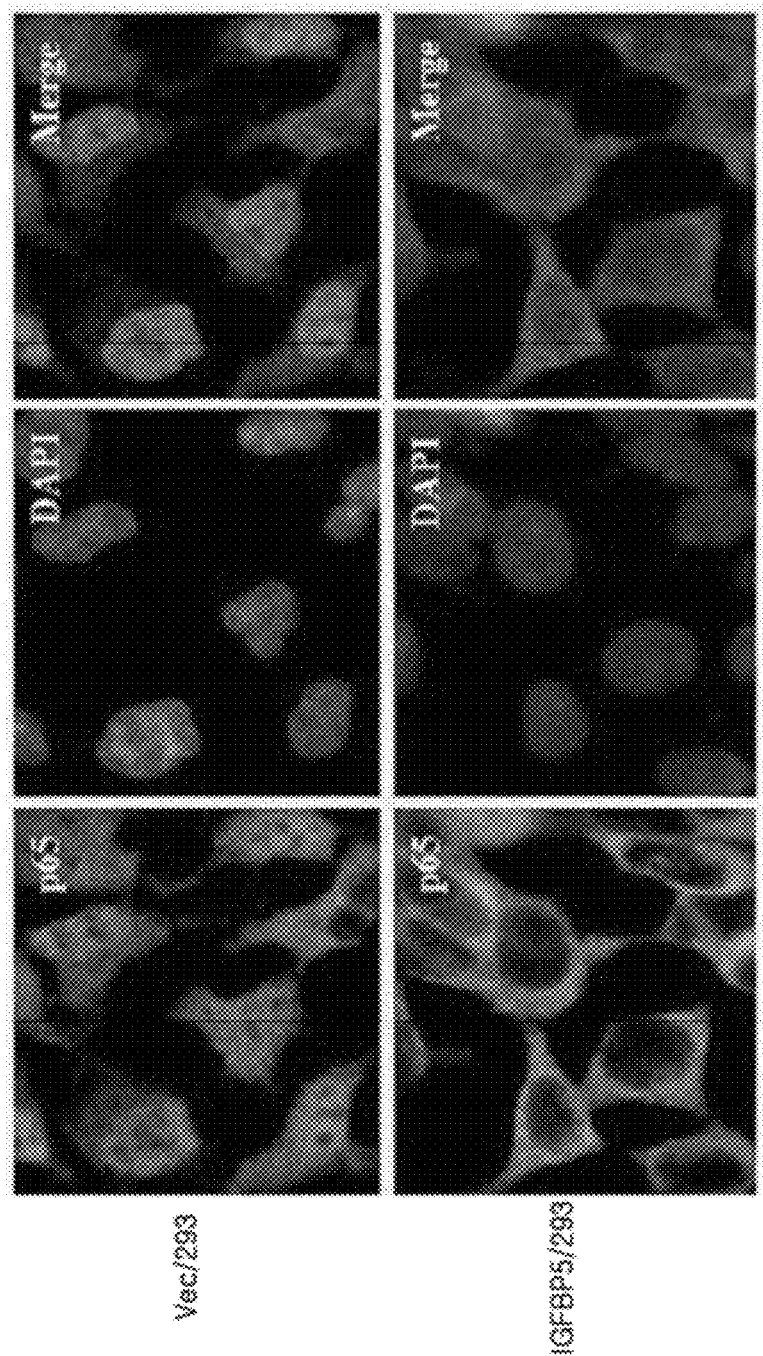
FIG. 12 shows the inhibition of IGFBP5 against TNF-α-induced NF-κB activation as a result of fluorescence microscopy for intracellular localization of p65, a subunit of NF-κB.
Figure 13:
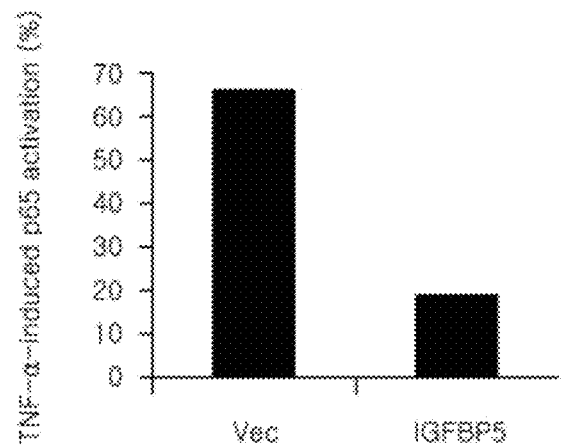
FIG. 13 is a bar graph showing the counts of the cells in which p65 of FIG. 12 translocated into the nuclei as percentages of the total counts of the cells.

To examine the effects of IGFBP5 as a competitive inhibitor of TNF-α on the downstream signaling of TNFR1, a test was conducted to see whether IGFBP5 inhibits the NF-κB signaling pathway activated by TNF-α. IGFBP5/293 stable cells were grown for 36 hours on collagen-coated cover-glass in E-well plates, washed twice with PBS, incubated for 2 hours in serum-free Opti-MEM, and treated for 2 hours with 100 ng/mL TNF-α. After fixation with 4% paraformaldehyde for 10 min, the cells were permabilized for 5 min with 0.1% Triton X-100, blocked with for 30 min with 3% BSA, stained for 1.5 hours with anti-p65 [NF-κB subunit; 1/250 dilution in dilution buffer (PBS containing 0.1% BSA, 0.05% Triton X-100)] and then for 1 hour with AlexaFluor-488 (1/2500 dilution in dilution buffer), and mounted for visualization under a fluorescence microscope. Typically, when activated by TNF-α, p65 translocates into the nucleus and promotes the transcription of genes necessary for cell growth therein. The nuclear translocation of p65 was detected in most of the Vec/293 cells treated with TNF-α whereas p65 was observed to remain in the cytoplasm of most of the IGFBP5/293 cells even when they were treated with TNF-α (FIG. 12). The counts of the cells in which p65 had translocated into the nucleus were numbered and are depicted as percentages of the total number of the cells. These results demonstrate that IGFBP5 acts as a competitive inhibitor of TNF-α for TNFR1 binding (FIG. 13).

Example 8

Inhibition of Secreted IGFBP5 Against PMA-induced NF-κB Activity

Figure 16:
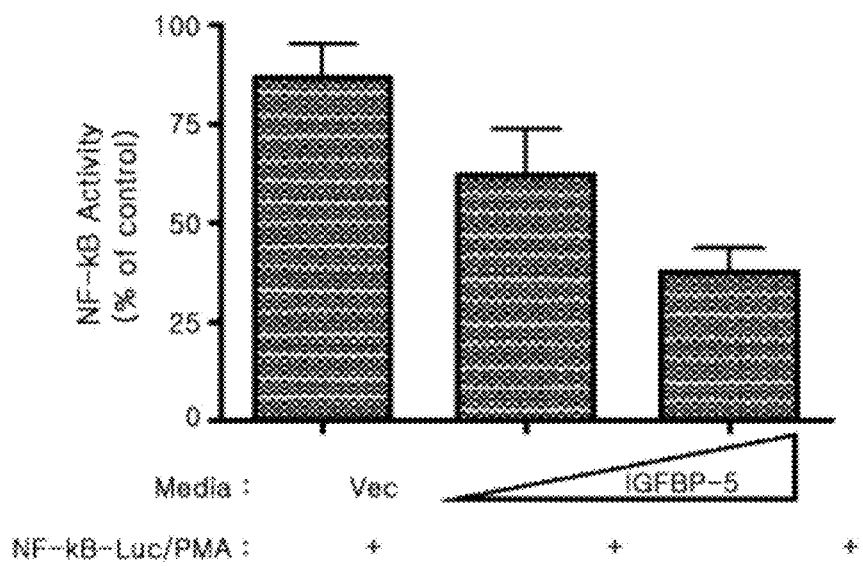
FIG. 16 shows a decrease in the activity of NF-κB with increasing levels of secreted IGFBP5 using a bar scale.

When treated with PMA (phorbol-12-myristate-13-acetate), the human myeloid cell line U-937 secretes cytokines such as TNF-α and IL-6. To study the inhibitory activity of IGFBP5 against PMA-induced NF-κB activity, U-937 cells were subjected overnight to serum starvation 24 hour after transient transfection with an NF-κB-dependent Luciferase reporter gene, and then treated for 3 hours with 25 ng/ml PMA. In this context, the conditioned media from IGFBP5/293 and Vec/293 stable cells were applied, together with PMA. The NF-κB activity was found to decrease with increasing amounts of the IGFBP5 conditioned media, as measured by NF-κB-dependent luciferase reporter assay (FIG. 16).

Upon activation by PMA, the expression level of IL-6, a downstream signal pathway of NF-κB, was measured using reverse-transcription PCR. After being subjected overnight to serum starvation, U-937 cells were treated for 6 hours with PMA (25 ng/ml), together with a Vec/293 conditioned medium or an IGFBP5/293 conditioned medium, followed by RNA isolation. As for the RNA isolation, it was performed using Trizol (Invitrogen Inc) according to the instruction of the manufacturer. cDNA was synthesized using Oligo-dT in the presence of Superscriptase II (Invitrogen Inc) and PCR was performed using ExTaq Polymerase (Solgent, South Korea). The PCR primer and PCR program employed were as follows.

```
IL-6 F: 5'-TGTAGCCGCCCCACACAGACAGCC-3'

IL-6 R: 5'-GAAGAGCCCTCAGGCTGGACTGC-3'
```

TABLE 1

| PCR Condition | cycle |
|---|---|
| 95° c. 2 min | |
| 95° c. 20 sec | 30 cycles |
| 65° c. 40 sec | |
| 72° c. 1 min | |
| 72° c. 5 min | |
| 40° c. ∞ | |

Figure 17:
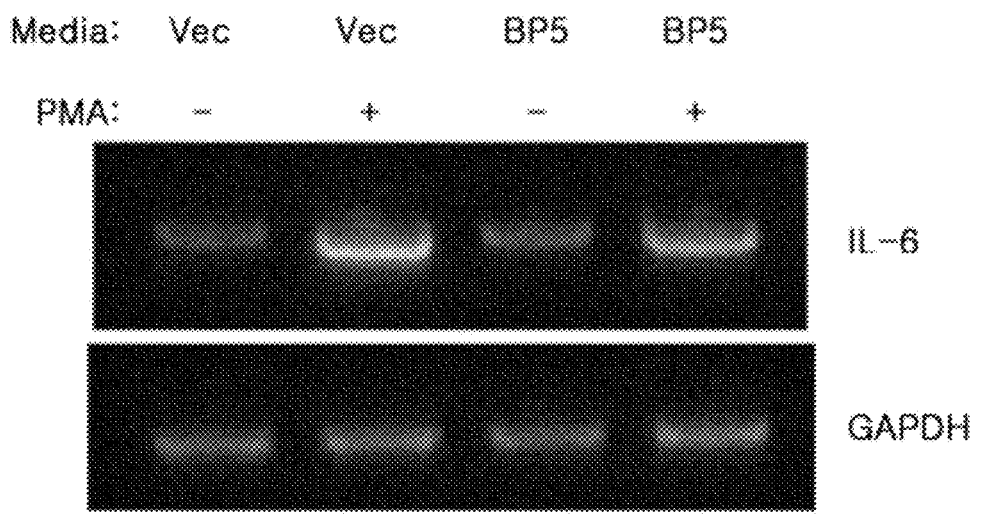
FIG. 17 shows a decrease in the NF-κB-dependent expression of IL-6, a downstream signal pathway of NF-κB, by about 40% in the conditioned medium containing IGFBP5.

PMA induced an increase in the expression level of IL-6 whereas the PMA-induced IL-6 gene expression was reduced by about 40% in the cells treated with the conditioned medium containing IFGBP5 (FIG. 17).

Figure 18:
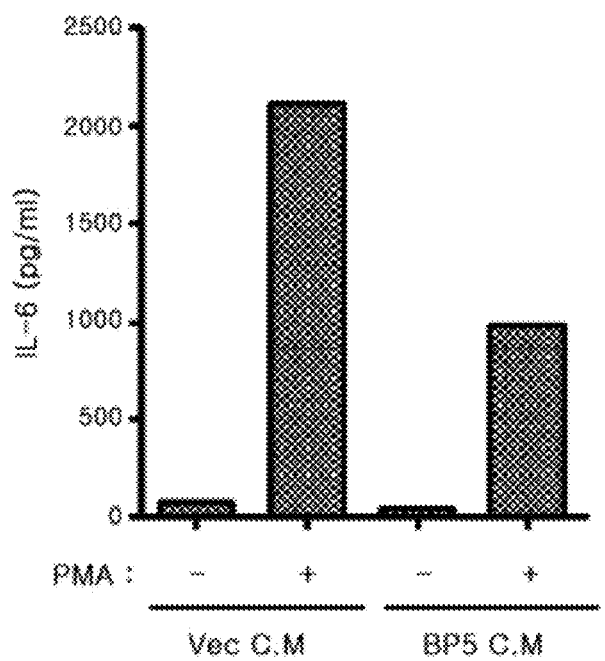
FIG. 18 confirms the result of FIG. 17 as result of ELISA for IL-6 on a bar scale.

The level of IL-6 in the media was measured by ELISA using Human IL-6 ELISA Kit II (BD Biosciences). The level of IL-6 in the media from the cells treated with PMA and the conditioned medium of IGFBP5/293 was reduced by 50%, compared to that in the media from the cells treated with PMA and the conditioned medium of Vec/293 (FIG. 18). These results demonstrate that IGFBP5 inhibits PMA-induced NF-κB signaling pathway in U-937 cells.

INDUSTRIAL APPLICABILITY

Functioning to block the binding of TNF-α to TNFR1, the composition of the IGFBP5 protein, the variant thereof or the fragment thereof in accordance with the present invention can be effective for the treatment of TNF-α overexpression-related diseases such as inflammatory diseases and cancer. In addition, the composition can be used safely without side effects of synthetic drugs because such IGFBP5 proteins are naturally present in the body.

What is claimed is:

1. The isolated TNF-α antagonist consisting of the amino acid sequence of SEQ ID NO: 4.

* * * * *

SEQUENCE LISTING

<160> NUMBER OF SEQ ID NOS: 4

<210> SEQ ID NO 1
<211> LENGTH: 819
<212> TYPE: DNA
<213> ORGANISM: Homo sapiens

<400> SEQUENCE: 1

```
atggtgttgc tcaccgcggt cctcctgctg ctggccgcct atgcggggcc ggcccagagc    60
ctgggctcct tcgtgcactg cgagccctgc gacgagaaag ccctctccat gtgcccccc    120
agcccctgg gctgcgagct ggtcaaggag ccgggctgcg gctgctgcat gacctgcgcc    180
ctggccgagg gcagtcgtg cggcgtctac accgagcgct cgcccaggg gctgcgctgc    240
ctcccccggc aggacgagga gaagccgctg cacgccctgc tgcacggccg cggggtttgc    300
ctcaacgaaa agagctaccg cgagcaagtc aagatcgaga gagactcccg tgagcacgag    360
gagcccacca cctctgagat ggccgaggag acctactccc ccaagatctt ccggcccaaa    420
cacacccgca tctccgagct gaaggctgaa gcagtgaaga aggaccgcag aaagaagctg    480
acccagtcca agtttgtcgg gggagccgag aacactgccc accccggat catctctgca    540
cctgagatga acaggagtc tgagcagggc ccctgccgca gacacatgga ggcttccctg    600
caggagctca agccagccc acgcatggtg ccccgtgctg tgtacctgcc caattgtgac    660
cgcaaaggat tctacaagag aaagcagtgc aaaccttccc gtggccgcaa acgtggcatc    720
tgctggtgcg tggacaagta cgggatgaag ctgccaggca tggagtacgt tgacggggac    780
tttcagtgcc acaccttcga cagcagcaac gttgagtga                          819
```

<210> SEQ ID NO 2
<211> LENGTH: 272
<212> TYPE: PRT
<213> ORGANISM: Homo sapiens

<400> SEQUENCE: 2

```
Met Val Leu Leu Thr Ala Val Leu Leu Leu Ala Ala Tyr Ala Gly
 1               5                  10                  15

Pro Ala Gln Ser Leu Gly Ser Phe Val His Cys Glu Pro Cys Asp Glu
            20                  25                  30

Lys Ala Leu Ser Met Cys Pro Pro Ser Pro Leu Gly Cys Glu Leu Val
        35                  40                  45

Lys Glu Pro Gly Cys Gly Cys Cys Met Thr Cys Ala Leu Ala Glu Gly
    50                  55                  60

Gln Ser Cys Gly Val Tyr Thr Glu Arg Cys Ala Gln Gly Leu Arg Cys
65                  70                  75                  80

Leu Pro Arg Gln Asp Glu Glu Lys Pro Leu His Ala Leu Leu His Gly
                85                  90                  95

Arg Gly Val Cys Leu Asn Glu Lys Ser Tyr Arg Glu Gln Val Lys Ile
            100                 105                 110

Glu Arg Asp Ser Arg Glu His Glu Glu Pro Thr Thr Ser Glu Met Ala
        115                 120                 125

Glu Glu Thr Tyr Ser Pro Lys Ile Phe Arg Pro Lys His Thr Arg Ile
    130                 135                 140

Ser Glu Leu Lys Ala Glu Ala Val Lys Lys Asp Arg Arg Lys Lys Leu
145                 150                 155                 160

Thr Gln Ser Lys Phe Val Gly Gly Ala Glu Asn Thr Ala His Pro Arg
                165                 170                 175
```

```
Ile Ile Ser Ala Pro Glu Met Arg Gln Glu Ser Glu Gln Gly Pro Cys
            180                 185                 190

Arg Arg His Met Glu Ala Ser Leu Gln Glu Leu Lys Ala Ser Pro Arg
            195                 200                 205

Met Val Pro Arg Ala Val Tyr Leu Pro Asn Cys Asp Arg Lys Gly Phe
            210                 215                 220

Tyr Lys Arg Lys Gln Cys Lys Pro Ser Arg Gly Arg Lys Arg Gly Ile
225                 230                 235                 240

Cys Trp Cys Val Asp Lys Tyr Gly Met Lys Leu Pro Gly Met Glu Tyr
                245                 250                 255

Val Asp Gly Asp Phe Gln Cys His Thr Phe Asp Ser Ser Asn Val Glu
            260                 265                 270

<210> SEQ ID NO 3
<211> LENGTH: 264
<212> TYPE: DNA
<213> ORGANISM: Artificial Sequence
<220> FEATURE:
<223> OTHER INFORMATION: IGFBP5 L-domain nucleotide sequence

<400> SEQUENCE: 3
ctcaacgaaa agagctaccg cgagcaagtc aagatcgaga gagactcccg tgagcacgag     60
gagcccacca cctctgagat ggccgaggag acctactccc ccaagatctt ccggcccaaa    120
cacacccgca tctccgagct gaaggctgaa gcagtgaaga aggaccgcag aaagaagctg    180
acccagtcca agtttgtcgg gggagccgag aacactgccc accccggat catctctgca     240 cctgagatga gacaggagtc tgag                                          264

<210> SEQ ID NO 4
<211> LENGTH: 88
<212> TYPE: PRT
<213> ORGANISM: Artificial Sequence
<220> FEATURE:
<223> OTHER INFORMATION: IGFBP5 L-domain amino acid sequence

<400> SEQUENCE: 4

Leu Asn Glu Lys Ser Tyr Arg Glu Gln Val Lys Ile Glu Arg Asp Ser
1               5                   10                  15

Arg Glu His Glu Glu Pro Thr Thr Ser Glu Met Ala Glu Glu Thr Tyr
            20                  25                  30

Ser Pro Lys Ile Phe Arg Pro Lys His Thr Arg Ile Ser Glu Leu Lys
            35                  40                  45

Ala Glu Ala Val Lys Lys Asp Arg Arg Lys Lys Leu Thr Gln Ser Lys
    50                  55                  60

Phe Val Gly Gly Ala Glu Asn Thr Ala His Pro Arg Ile Ile Ser Ala
65                  70                  75                  80

Pro Glu Met Arg Gln Glu Ser Glu
                85
```